United States Patent [19]

Poduslo et al.

[11] Patent Number: 5,604,198

[45] Date of Patent: Feb. 18, 1997

[54] METHOD TO ENHANCE PERMEABILITY OF THE BLOOD/BRAIN BLOOD/NERVE BARRIERS TO THERAPEUTIC AGENTS

[76] Inventors: Joseph F. Poduslo, 5719 St. Mary's Dr. NW., Rochester, Minn. 55901; Geoffrey L. Curran, 629 23rd St. NE., Rochester, Minn. 55906

[21] Appl. No.: 241,621

[22] Filed: May 12, 1994

[51] Int. Cl.$^6$ ..................................................... A61K 38/16
[52] U.S. Cl. .................................... 514/6; 514/8; 514/12; 514/21; 530/327; 424/94.2
[58] Field of Search ............................. 514/6, 8, 12, 21; 530/327; 424/94.2

[56] References Cited

U.S. PATENT DOCUMENTS

| | | | |
|---|---|---|---|
| 3,903,262 | 9/1975 | Pappenhagen et al. | 424/85 |
| 4,863,730 | 9/1989 | Karpas | 424/86 |
| 5,260,308 | 11/1993 | Poduslo et al. | 514/21 |
| 5,304,632 | 4/1994 | Vaudry et al. | 530/327 |
| 5,360,610 | 11/1994 | Tice et al. | 424/426 |
| 5,442,043 | 8/1995 | Fukuta et al. | 530/303 |

FOREIGN PATENT DOCUMENTS 618555  8/1987  Australia.

OTHER PUBLICATIONS

Meijer, D. F. K. et al, Antiviral Res., vol. 18, pp. 215–258, 1992.
Fiani, Maria et al., TIBTECH, vol. 7, pp. 57–61, Mar. 1989.
Pardridge, William TIBTECH, vol. 12, pp. 239–245, Jun. 1994.
Patel N. J. et al., Diabetologia, vol. 34, pp. 78–80, 1991.
Zlohovic, J Controlled Res., vol. 13, pp. 185–201, 1990.
Stern et al., Arch. int. Pharmacodyn., vol. 202, pp. 259–262, 1973.
Andersson et al., "Synthesis of oligosaccharides with oligoethylene glycol spacers and their conversion into glycoconjugates using N,N, N',N"tetramethyl (succinimido)uronium tetrafluoroborate as coupling reagent," *Glycoconjugate Journal*, 10, 197 (1993).
Barbin et al., "Purification of the Chick Eye Ciliary Neuronotrophic Factor," *J. Neurochem.*, 43, 1468 (1984).
Barde et al., "Purification of a new neurotrophic factor from mammalian brain," *EMBO J.*, 1, 549 (1982).
J. Barnett et al., "Human Nerve Growth Factor Obtained from a Baculovirus Expression System Has Potent in Vitro and in Vivo Neurotrophic Activity," *Exp. Neurol.*, 110:11 (1990).
D. Baskin et al., "Insulin in the Brain," *Ann. Rev. Physiol.*, 49, 335 (1987).
D. Baskin et al., "Insulin and Insulin–Like Growth FActors in the CNS," *Trends in Neurosciences*, 11, 107 (1988).
S. Berkman et al., "Clinical Uses of Intravenous Immunoglobulins," *Ann. Int. Med.*, 112:278 (1990).
Bovin et al., "Synthesis of polymeric neoglycoconjugates based on N–Substituted polyacrylamides," *Glycoconjugate Journal*, 10, 142 (1993).

M. Brownlee et al., "Trapped Immunoglobulins on Peripheral Nerve Myeline from Patients with Diabetes Mellitus," *Diabetes*, 35:999 (1986).
Bunn et al., "Reaction of Monosaccharides with Proteins: Possible Evolutionary Significance," 213, 222 (1991).
D. Cook et al., "High–dose Intravenous Immunoglobulin in the Treatment of Demyelinating Neuropathy Associated with Monoclonal Gammopathy," *Neurology*, 40:212 (1990).
L. Curtiss et al., "A Novel Method for Generating Region–Specific Monoclonal Antibodies to Modified Proteins," *J. Clin. Invest.*, 72:1427 (Oct. 1983).
W. Fischer et al., "Amelioration of Cholineragic Neuron Atrophy and Spatial Memory Impairment in Aged Rats for Nerve Growth Factor," *Nature*, 329:65 (1987).
Hefti et al., "Function of Neurotrophic Factors in the Adult and Aging Brain and Their Possible Use in the Treatment of Neurodegenerative Diseases," *Neurobiology of Aging*, 10, 515 (1989).
A. Karpas et al., "Effects of Passive Immunization in Patients with the Acquired Immunodeficiency Syndrome–Related Complex and Acquired Immunodeficiency Syndrome," *PNAS USA*, 85:9234 (1988).
Knusel et al., "Brain–derived Neurotrophic Factor Administration Protects Basal Forebrain Cholinergic but Not Nigral Dopaminergic Neurons from Degenerative Changes after Axotomy in the Adult Rat Brain," *J. Neurosci. Res.*, 12(11):4391 (1992).
Koliatsos et al., "Evidence That Brain–Derived Neurotrophic Factor is a Trophic Factor for Motor Neurons In Vivo," *Neuron*, 10, 359 (1993).
A. LeBlanc et al., "Regulation of Apolipoprotein E. Gene Expression After Injury of the Rat Sciatic Nerve," *J. Neuroscience Res.*, 25:162 (1990).
P. Lipsky et al., "Intravenous Immunoglobulin. Prevention and Treatment of Disease," *JAMA*, 264:3189 (1990).
Louis et al., "CNTF Protection of Oligodendrocytes Against Natural and Tumor Necrosis Factor–Induced Death," *Science*, 259, 689 (1993).
Meakin et al., "The nerve growth factor family of receptors," *TINS*, 15 323 (1992).
J. Poduslo et al., "Increased permeability across the blood–nerve barrier of albumin glycated in vitro and in vivo from patients with diabetic polyneuropathy," *PNAS USA*, 89, 2218 (1992).

(List continued on next page.)

*Primary Examiner*—Chhaya D. Sayala
*Attorney, Agent, or Firm*—Schwegman, Lundberg, Woessner & Kluth, P.A.

[57] ABSTRACT

A method is provided to enhance the ability of a neurologically active compound to penetrate the blood nerve barrier (BNB) or blood brain barrier (BBB), by administration of a conjugate comprising the neurologically active compound linked to a carrier molecule that has been shown to have a substantial permeability coefficient across the BNB and BBB.

19 Claims, No Drawings

OTHER PUBLICATIONS

J. Poduslo, "Glycoprotein Molecular–Weight Estimation Using Sodium Dodecyl Sulfate–Pore Gradient Electrophoresis: Comparison of the Tris–Glycine and Tris–Borate–EDTA Buffer Systems," *Anal. Biochem.*, 114, 131 (1981).

J. Poduslo et al., "Altered Blood–Nerve Barrier in Experimental Lead Neuropathy Assessed by Changes in Endoneurial Albumin Concentration," *J. Neurosci.*, 2, 1507 (1982).

J. Poduslo et al., "Mammalian Endoneurial Fluid: Collection and Protein Analysis from Normal and Crushed Nerves," *Brain Res.*, 332, 91 (1985).

J. Poduslo et al., "Increase in Albumin IgG, and IgM Blood–Nerve Barrier Indices in Human Diabetic Neuropathy," *PNAS USA*, 85:4879 (1988).

Pozsgay, "A method for glycoconjugate synthesis," *Glycoconjugate Journal*, 10, 133 (1993).

E. Rechthand et al., "Regulation of the Microenvironment of Peripheral Nerve: Role of the Blood–Nerve Barrier," *Progress in Neurobiology*, 28:303 (1987).

M. Scwhartz et al., "Kinetics and Specificity of Insulin Uptake from Plasma into Cerebrospinal Fluid," *Am. J. Physiol.*, 259:E378 (1990).

Sendtner et al., "Brain–derived neurotrophic factor prevents the death of motoneurons in newborn rats after nerve section," *Nature*, 360, 757 (1992).

N. Shaklai et al., "Nonenzymatic Glyosylation of Human Serum Albumin Alters its Conformation and Function," *J. Biol. Chem.*, 259:3812 (1984).

P. Smith et al., "Measurement of Protein Using Bicinchoninic Acid," *Anal. Biochem.*, 150, 76 (1985).

Smith et al, "Nonenzymic Glycation of Albumin by Acyl Glucuronides In Vitro," *Biochemical Pharmacology*, 44, 1661 (1992).

Swamy et al., "Glycation Mediated Lens Crystallin Aggregation and Crosslinking by Various Sugar Phosphates In Vitro" *Exp. Eye Res.*, 56, 177 (1993).

Szwergold et al., "Identification of Fructose 3–Phosphate in the Lens of Diabetic Rats," *Science*, 247 451 (1990).

J. Tarsio et al., "Nonenzymatic Glycation of Fibronectin and Alterations in the Molecular Association of Cell Matrix and Basement Membrane Components in Diabetes Mellitus," *Diabetes*, 34, 477 (1985).

J. Tarsio et al., "Decreased Interaction of Fibronectin, Type IV Collagen and Heparin Due to Nonenzymatic Glycation. Implications for Diabetes Mellitus," *Biochemistry*, 26, 1014 (1987).

P. Van Doorn et al., "On the Mechanism of High–Dose Intravenous Immunoglobulin Treatment of Patients with Chronic Inflammatory Demyelinating Polyneuropathy," *J. Neuroimmunol.*, 29:57 (1990).

Watters et al., "Purification of Ciliary Neurotrophic Factor from Bovine Heart," *J. Neurochem.*, 49, 705 (1987).

A. Weerasuriya et al., "Blood–Nerve Transfer of Albumin and Its Implications for the Endoneurial Microenvironment," *Brain Res.*, 494, 114 (1989).

Wong et al., "Synthetic glycosylation of peptides using unprotected saccharide β–glycosylamines," *Glycoconjugate Journal*, 10, 227 (1993).

Yan et al., "Brain–derived neurotrophic factor rescues spinal motor neurons from axotomy–induced cell death," *Nature*, 360, 753 (1992).

METHOD TO ENHANCE PERMEABILITY OF THE BLOOD/BRAIN BLOOD/NERVE BARRIERS TO THERAPEUTIC AGENTS

This invention was made with the support of the National Institutes of Health under grant number NS 14304-P4. The U.S. Government has certain rights in the invention.

BACKGROUND OF THE INVENTION

The interstitial connective tissue in the peripheral nerve that separates the individual nerve fibers of a vertebrate is referred to as the endoneurium, and can be visualized as an insulative medium in which conductive wires are embedded. Blood vessels in the endoneurium of peripheral nerves are comparable to those of the central nervous system and are lined by a continuous endothelium, made up of capillary endothelial cells, with intercellular tight junctions of high electrical resistance (100 ohm/cm$^2$). Together with the perineurium, a connective tissue sheath immediately surrounding the fascicles of nerve fibers, the vessels form a blood-nerve barrier (BNB) to regulate the microenvironment of the endoneurium of the nerve. The blood-cerebrospinal fluid barrier and the blood brain barrier (collectively the "BBB") are also associated with the tight junctions which adjoin adjacent capillary endothelial cells within the brain and spinal cord, to regulate this microenvironment as well.

The BNB and BBB are effective barriers to both endogenous and exogenously-administered blood components, including peptides, proteins and other large macromolecules, as well as to ions and water-soluble non-electrolytes. This protects the brain or endoneurial microenvironment from rapid changes in the composition of the blood or of the extraneural spaces. Also, alterations in BBB or BNB integrity are implicated in a number of brain and peripheral nerve disorders, such as those caused by diabetes mellitus, toxins, infection and autoimmune disorders.

However, the ability of the BNB and BBB to protect the nervous system from exogenous substances has impeded the development of both diagnostic assays and therapies for a wide variety of neural pathologies and disorders. Thus, a continuing need exists for methods to increase the permeability of the BNB or the BBB to bioactive substances, particularly to bioactive peptides and proteins.

SUMMARY OF THE INVENTION

The present invention provides a method to enhance the ability of a neurologically active compound to penetrate the blood nerve barrier (BNB) or blood brain barrier (BBB). The method comprises parenterally administering to a mammal, preferably a human, in need of treatment with said neurologically active compound, a conjugate consisting of an effective amount of said neurologically active compound conjugated to a carrier molecule which enhances the permeability of the BNB or BBB to said neurologically active agent. Preferably the method of the present invention will employ hemoglobin, lysozyme, cytochrome c, ceruloplasmin, calmodulin, ubiquitin or substance P as the carrier molecule. Most preferably, the method of the present invention will employ substance P, calmodulin or ubiquitin as the carrier molecule.

A wide variety of neurologically active compounds can be transported across the BNB or BBB, to affect the central nervous system (CNS) or the peripheral nervous system (PNS) of the mammal to be treated. For example, the neurologically active compound can be selected from the group consisting of a compound acting at synaptic and/or neuroeffector junctional sites, a compound acting on the central or peripheral nervous systems, or a neurotrophic protein. Preferably, the method of the present invention will employ a neurotrophic protein as the neurologically active agent.

Although there could be a plurality of neurologically active compounds conjugated to any given carrier molecule, preferably, the conjugate comprises an about 1:1 molar ratio of the neurologically active compound and the carrier. Preferably, the conjugate is used in combination with a pharmaceutically acceptable carrier, such as a carrier adapted for parenteral administration. Preferably, the pharmaceutically acceptable carrier is a liquid vehicle.

DETAILED DESCRIPTION OF THE INVENTION

A. Neurologically Active Agents

Neurologically active agents which can be introduced into the nervous system, i.e., into the endoneurial or brain microenvironment, in accord with the present method, include any bioactive agent which can be purified and conjugated or cross-linked to the carrier protein, so that its ability to cross the BNB or BBB is substantially enhanced over the nonconjugated form of the therapeutic agent. The term "substantially enhanced" or "enhanced" is to be understood in the context of the increases in the permeability across the BNB or the BBB observed for conjugated therapeutic agents over that observed for the nonconjugated forms, i.e., an at least about 5–20-fold increase measured by the methodologies disclosed herein. As used herein with respect to the conjugated therapeutic agents useful in the present method, the term "neurologically active" or "neuroactive" means that the "neurologically active" agent exerts a direct or indirect beneficial therapeutic effect upon introduction into the nervous system, e.g., by stimulating nerve growth or activity, neutralizing a pathogen, relieving pain, affecting a psychological state, inhibiting neoplastic cell growth and the like.

1. Neurologically Active Agents Acting at Synaptic and Neuroeffector Junction Sites The neurologically active agent useful in the present conjugate may be one that acts at the synaptic and neuroeffector junctional sites; such as a cholinergic agonist, a anticholinesterase agent, catecholamine and other sympathomimetic drugs, an adrenergic receptor antagonist, an antimuscarinic drug, and an agent that act at the neuromuscular junction and autonomic ganglia.

a. Cholinergic Agonists

Examples of suitable cholinergic agonists include, but are not limited to, choline chloride, acetylcholine chloride, methacholine chloride, carbachol chloride, bethanechol chloride, pilocarpine, muscarine, arecoline and the like. See Taylor, P., in *The Pharmacological Basis of Therapeutics*, Gilman, et al., eds., Pergamon Press, New York, 1990, 8th edition, Chapter 6, pp. 122–130.

b. Anticholinesterase Agents

Suitable anticholinesterase agents are exemplified by the group consisting of carbaril, physostigmine, neostigmine, edrophonium, pyridostigmine, demecarium, ambenonium, tetrahydroacridine and the like. See Taylor, P., in *The Pharmacological Basis of Therapeutics*, Gilman, et al., eds., Pergamon Press, New York, 1990, 8th edition, Chapter 7, pp. 131–149.

c. Catecholamines and other Sympathomimetic Therapeutic Agents

Suitable catecholamines and sympathomimetic drugs include the subclasses of endogenous catecholamines, β-adrenergic agonists, α-adrenergic agonists and other miscellaneous adrenergic agonists.

Within the subclass of endogenous catecholamines, suitable examples include epinephrine, norepinephrine, dopamine and the like. Suitable examples within the subclass of β-adrenergic agonists include, but are not limited to, isoproterenol, dobutamine, metaproterenol, terbutaline, albuterol, isoetharine, pirbuterol, bitolterol, ritodrine and the like. The subclass of α-adrenergic agonists can be exemplified by methoxamine, phenylephrine, mephentermine, metaraminol, clonidine, guanfacine, guanabenz, methyldopa and the like. Other miscellaneous adrenergic agents include, but are not limited to, amphetamine, methamphetamine, methylphenidate, pemoline, ephedrine and ethylnorepinephrine and the like. See Hoffman et al., in *The Pharmacological Basis of Therapeutics*, Gilman, et al., eds., Pergamon Press, New York, 1990, 8th edition, Chapter 10, pp. 187–220.

d. Adrenergic Receptor Antagonists

Adrenergic receptor antagonists include the subclasses of α-adrenergic receptor antagonists and β-adrenergic receptor antagonists. Suitable examples of neurologically active agents that can be classified as α-adrenergic receptor antagonists include, but are not limited to, phenoxybenzamine and related haloalkylamines, phentolamine, tolazoline, prazosin and related drugs, ergot alkaloids and the like. Either selective or nonselective β-adrenergic receptor antagonists are suitable for use in the present invention, as are other miscellaneous β-adrenergic receptor antagonists. See Hoffman et al., in *The Pharmacological Basis of Therapeutics*, Gilman, et al., eds., Pergamon Press, New York, 1990, 8th edition, Chapter 11, pp. 221–243.

e. Antimuscarinic Therapeutic Agents

Antimuscarinic drugs are exemplified by the group consisting of atropine, scopolamine, homatropine, belladonna, methscopolamine, methantheline, propantheline, ipratropium, cyclopentolate, tropicamide, pirenzepine and the like. See Brown, J. H., in *The Pharmacological Basis of Therapeutics*, Gilman, et al., eds., Pergamon Press, New York, 1990, 8th edition, Chapter 8, pp. 150–165.

f. Agents that act at the Neuromuscular Junction and Autonomic Ganglia

Suitable examples of neurologically active agents that can be classified as agents that act at the neuromuscular junction and autonomic ganglia include, but are not limited to, tubocurarine, alcuronium, β-Erythroidine, pancuronium, gallamine, atracurium, decamethonium, succinylcholine, nicotine, labeline, tetramethylammonium, 1,1-dimethyl-4-phenylpiperazinium, hexamethonium, pentolinium, trimethaphan and mecamylamine, and the like. See Taylor, P., in *The Pharmacological Basis of Therapeutics*, Gilman, et al., eds., Pergamon Press, New York, 1990, 8th edition, Chapter 8, pp. 166–186.

2. Drugs Acting on the Central Nervous System and the Peripheral Nervous System

The neurologically active agent of the present invention may also be one that acts on the central nervous system (CNS) and peripheral nervous system (PNS), such as nonpeptide neurotransmitters, peptide neurotransmitters and neurohormones, proteins associated with membranes of synaptic vessels, neuromodulators, neuromediators, sedative-hypnotics, antiepileptic therapeutic agents, therapeutic agents effective in the treatment of Parkinsonism and other movement disorders, opioid analgesics and antagonists and antipsychotic compounds.

a. Nonpeptide Neurotransmitters

Nonpeptide neurotransmitters include the subclasses of neutral amino acids—such as glycine and gamma-aminobutyric acid and acidic amino acids—such as glutamate, aspartate, and NMDA receptor antagonist-MK801 (Dizocilpine Maleate). L. L. Iversen, Neurotransmissions, Research biochemicals Internation, Vol. X, no. 1, February 1994. Other suitable nonpeptide neurotransmitters are exemplified by acetylcholine and the subclass of monoamines—such as dopamine, norepinephrine, 5-hydroxytryptamine, histamine, and epinephrine.

b. Neurotransmitters and Neurohormones—Neuroactive Peptides

Neurotransmitters and neurohormones that are neuroactive peptides include the subclasses of hypothalamic-releasing hormones, neurohypophyseal hormones, pituitary peptides, invertebrate peptides, gastrointestinal peptides, those peptides found in the heart—such as atrial naturetic peptide, and other neuroactive peptides. See J. H. Schwartz, "Chemical Messengers: Small Molecules and Peptides" in *Principles of Neural Science*, 3rd Edition; E. R. Kandel et al., Eds.; Elsevier: New York; Chapter 14, pp. 213–224 (1991).

The subclass of hypothalamic releasing hormones includes as suitable examples, thyrotropin-releasing hormones, gonadotropin-releasing hormone, somatostatins, corticotropin-releasing hormone and growth hormone-releasing hormone.

The subclass of neurohypophyseal hormones is exemplified by agents such as vasopressin, oxytocin, and neurophysins. Likewise the subclass of pituitary peptides is exemplified by the group consisting of adrenocorticotropic hormone, β-endorphin, α-melanocyte-stimulating hormone, prolactin, luteinizing hormone, growth hormone, and thyrotropin.

Suitable invertebrate peptides are exemplified by the group comprising FMRF amide, hydra head activator, proctolin, small cardiac peptides, myomodulins, buccolins, egg-laying hormone and bag cell peptides. The subclass of gastrointestinal peptides includes such therapeutic agents as vasoactive intestinal peptide, cholecystokinin, gastrin, neurotensin, methionine-enkephalin, leucine-enkephalin, insulin and insulin-like growth factors I and II, glucagon, peptide histidine isoleucineamide, bombesin, motilin and secretins.

Suitable examples of other neuroactive peptides include angiotensin II, bradykinin, dynorphin, opiocortins, sleep peptide(s), calcitonin, CGRP (calcitonin gene-related peptide), neuropeptide Y, neuropeptide Yy, galanin, substance K (neurokinin), physalaemin, Kassinin, uperolein, eledoisin and atrial naturetic peptide.

c. Proteins associated with Membranes of Synaptic Vesicles

Proteins associated with membranes of synaptic vesicles include the subclasses of calcium-binding proteins and other synaptic vesicle proteins.

The subclass of calcium-binding proteins further includes the cytoskeleton-associated proteins—such as caldesmon, annexins, calelectrin (mammalian), calelectrin (torpedo), calpactin I, calpactin complex, calpactin II, endonexin I, endonexin II, protein II, synexin I; and enzyme modulators—such as p65.

Other synaptic vesicle proteins include inhibitors of mobilization (such as synapsin Ia,b and synapsin IIa,b), possible fusion proteins such as synaptophysin, and proteins of unknown function such as p29, VAMP-1,2 (synaptobrevin), VAT-1, rab 3A, and rab 3B. See J. H. Schwartz, "Synaptic Vessicles" in *Principles of Neural Science*, 3rd Edition; E. R. Kandel et al., Eds.; Elsevier: New York; Chapter 15, pp. 225–234(1991).

d. Neuromodulators

Neuromodulators can be exemplified by the group consisting of $CO_2$ and ammonia (E. Flory, *Fed. Proc.*, 26, 1164–1176 (1967)), steroids and steroid hormones (C. L. Coascogne et al., *Science*, 237, 1212–1215 (1987)), adenosine and other purines, and prostaglandins.

e. Neuromediators

Neuromediators can be exemplified by the group consisting of cyclic AMP, cyclic GMP (F. E. Bloom, *Rev. Physiol. Biochem. Pharmacol.*, 74, 1–103 (1975), and cyclic nucleotide-dependent protein phosphorylation reactions (P. Greengard, *Distinguished Lecture Series of the Society of General Physiologists*, 1, Raven Press: New York (1978)).

f. Sedative-Hypnotics

Sedative-hypnotics can be exemplified by the group consisting of benzodiazepines and buspirone, barbiturates, and miscellaneous sedative-hypnotics. A. J. Trevor and W. L. Way, "Sedative-Hypnotics" in *Basic and Clinical Pharmacology*; B. G. Katzung, Ed.; Appleton and Lange; Chapter 21, pp. 306–319 (1992).

g. Antiepileptic Therapeutic Agents

Suitable antiepileptic drugs can be exemplified by the groups consisting of, but not limited to, hydantoins such as phenytoin, mephenytoin, and ethotoin; anticonvulsant barbiturates such as phenobarbital and mephobarbital; deoxybarbiturates such as primidone; iminostilbenes such as carbamazepine; succinimides such as ethosuximide, methsuximide, and phensuximide; valproic acid; oxazolidinediones such as trimethadione and paramethadione; benzodiazepines and other antiepileptic agents such as phenacemide, acetazolamide, and progabide. See T. W. Rallet al., "Drugs Effective in the Therapy of the Epilepsies", in *The Pharmacological Basis of Therapeutics*, 8th Edition; A. G. Gilman et al., Eds.; Pergamon Press: New York; Chapter 19, pp. 436–462 (1990).

h. Parkinsonism and other Movement Disorders

Neurologically active agents that are effective in the treatment of Parkinsonism and other movement disorders include, but are not limited to, dopamine, levodopa, carbidopa, amantadine, baclofen, diazepam, dantrolene, dopaminergic agonists such as apomorphine, ergolines such as bromocriptine, pergolide, and lisuride, and anticholinergic drugs such as benztropine mesylate, trihexyphenidyl hydrochloride, procyclidine hydrochloride, biperiden hydrochloride, ethopropazine hydrochloride, and diphenhydramine hydrochloride. See J. M. Cedarbaum et al., "Drugs for Parkinson's Disease, Spasticity, and Acute Muscle Spasms", in *The Pharmacological Basis of Therapeutics*, 8th Edition; A. G. Gilman et al., Eds.; Pergamon Press: New York; Chapter 20, pp. 463–484 (1990).

i. Opioid Analgesics and Antagonists

Suitable opioid analgesics and antagonists can be exemplified by the group consisting of, but not limited to, endogenous opioid peptides such as enkephalins, endorphins, and dynorphins; morphine and related opioids such as levorphanol and congeners; meperidine and congeners such as piperidine, phenylpiperidine, diphenoxylate, loperamide, and fentanyl; methadone and congeners such as methadone and propoxyphene; pentazocine; nalbuphine; butorphanol; buprenorphine; meptazinol; opioid antagonists such as naloxone hydrochloride; and centrally active antitussive agents such as dextromethorphan. See J. H. Jaffe et al., "Opioid Analgesics and Antagonists" in *The Pharmacological Basis of Therapeutics*, 8th Edition; A. G. Gilman et al., Eds.; Pergamon Press: New York; Chapter 21, pp. 485–521 (1990)

j. Antipsychotic Compounds

Neurologically active agents that can be used to treat depression, anxiety or psychosis are also useful in the present conjugate. Suitable antipsychotic compounds include, but are not limited to, phenothiazines, thioxanthenes, dibenzodiazepines, butyrophenones, diphenylbutylpiperidines, indolones, and rauwolfia alkaloids. Mood alteration drugs that are suitable for use in the present invention include, but are not limited to, tricyclic antidepressants (which include tertiary amines and secondary amines), atypical antidepressants, and monoamine oxidase inhibitors. Examples of suitable drugs that are used in the treatment of anxiety include, but are not limited to, benzodiazepines. R. J. Baldessarini, "Drugs and the Treatment of Psychiatric Disorders", in *The Pharmacological Basis of Therapeutics*, 8th Edition; A. G. Gilman et al., Eds.; Pergamon Press: New York; Chapter 18, pp. 383–435 (1990).

3. Neuroactive Proteins

The neurologically active agent useful in the present conjugate may also be a neuroactive protein, such as human and chimeric mouse/human monoclonal antibodies, erythropoietin and G-CSF, orthoclone OKT3, interferon-gamma, interleukin-1 receptors, t-PA (tissue-type plasminogen activator), recombinant streptokinase, superoxide dismutase, tissue factor pathway inhibitor (TFPI). See *Therapeutic Proteins: Pharmacokinetics and Pharmacodynamics*; A. H. C. Kung et al., Eds.; W. H. Freeman: New York, pp 1–349 (1993).

4. Neuroactive Nonprotein Drugs

The neurologically active agent useful in the present conjugate may also be a neuroactive nonprotein drug, such as neurotransmitter receptors and pharmacological targets in Alzheimer's disease; Design and Synthesis of BMY21502: A Potential Memory and Cognition Enhancing Agent; muscarinic agonists for the central nervous system; serotonic receptors, agents, and actions; thiazole-containing 5-hydroxytryptamine-3 receptor antagonists; acidic amino acids as probes of glutamate receptors and transporters; L-2-(carboxycyclopropyl)glycines; and N-Methyl-D-aspartic acid receptor antagonists. See *Drug Design for Neuroscience*; A. P. Kozikowski, Ed.; Raven Press: New York, pp 1–469 (1993).

5. Approved Biotechnology Drugs or Biotechnology Drugs in Development

The neurologically active agent useful in the present conjugate may also be an approved biotechnology drug or a biotechnology drug in development. Exemplary members of this group are included on Tables 1 and 2 (approved biotechnology drugs and biotechnology drugs in development, respectively) and may be found in J. E. Talmadge, *Advanced Drug Delivery Reviews*, 10, 247–299 (1993).

TABLE 1

APPROVED BIOTECHNOLOGY DRUGS

| Approved Drugs Product Type | Abbreviated Indication | Date Approved |
|---|---|---|
| Interferon-gamma 1b | Chronic granulomatous disease | Dec. 1990 |
| Interferon-alpha-n | Genital warts | Oct. 1989 |
| Epoetin-alpha | Anemia of chronic renal failure | June 1989 |
| Epoetin-alpha | Anemia of chronic renal failure | Dec. 1990 |

TABLE 1-continued

APPROVED BIOTECHNOLOGY DRUGS

| Approved Drugs Product Type | Abbreviated Indication | Date Approved |
|---|---|---|
| Interferon-alpha-2b | Hairy cell leukemia | June 1986 |
| | Genital warts | June 1986 |
| | AIDS-related Kaposi's sarcoma | Nov. 1988 |
| | Non-A and non-B hepatitis | Feb. 1991 |
| Sargramostin (CSF-GM) | Autologous bone marrow transplant | March 1991 |
| Sargramostin (CSF-GM) | Autologous bone marrow transplant | March 1991 |

TABLE 1-continued

APPROVED BIOTECHNOLOGY DRUGS

| Approved Drugs Product Type | Abbreviated Indication | Date Approved |
|---|---|---|
| Filgrastim (r-CSF-G) | Chemotherapy-induced neutropenia | Feb. 1991 |
| Interferon-alpha-2a | Hairy cell leukemia | June 1986 |
| | AIDS-related Kaposi's sarcoma | Nov. 1988 |
| Aldesleukin (IL-2) | Renal cell carcinoma | May 1992 |

TABLE 2

BIOTECHNOLOGY DRUGS IN DEVELOPMENT

| Approved Drugs Product Type | Abbreviated Indication | U.S. Status |
|---|---|---|
| Colony-stimulating factors | | |
| CSF-GM | Adjuvant to chemotherapy | Phase I/II |
| CSF-GM | Low blood cell counts | Submitted |
| sargramostim (CSF-GM) | Allogeneic bone marrow transplants, chemotherapy adjuvant | Phase III |
| | Adjuvant to AIDS therapy | Phase II |
| CSF-M | Cancer, fungal disease | Phase I |
| CSF-M | Cancer, hematologic neoplasms, bone marrow transplants | Phase I |
| Filgrastim (r-CSF-G) | AIDS, leukemia aplastic anemia | Submitted |
| Sargramostim (CSF-GM) | Neutropenia to secondary chemotherapy | Phase III |
| Erythroproietins | | |
| Epoetin-beta | Anemia secondary to kidney disease | Submitted |
| | Autologous transfusion | Phase II/III |
| Epoetin-alpha | Anemia of cancer and chemotherapy | Submitted |
| | Anemia of surgical blood loss, autologous transfusion | Phase III |
| Interferons | | |
| Interferon-gamma-1b | Small-cell lung cancer, atop dermatitis | Phase III |
| | Trauma-related infections, renal cell carcinoma | Phase II |
| | Asthma and allergies | Phase I |
| Interferon-alpha-n3 | ARC, AIDS | Phase I/II |
| Interferon-beta | Multiple sclerosis | Phase III |
| | Cancer | Phase I/II |
| Interferon-gamma | Rheumatoid arthritis | Phase II/III |
| | Venereal warts | Phase II |
| Interferon consensus | Cancer, infectious disease | Phase II/III |
| Interferon-gamma | Cancer, infectious disease | Phase II |
| Interferon-alpha-2b | Superficial bladder cancer, basal cell carcinoma, chronic hepatitis B, delta hepatitis | Submitted |
| | Acute hepatitis B, delta hepatitis, acute chronic myelogenous leukemia | Phase III |
| | HIV (with Retrovir) | Phase I |
| Interferon-beta | Unresponsive malignant disease | Phase I |
| Interferon-alpha-2a | colorectal cancer (with 5-fluorouracil); chronic, acute hepatitis B; non-A, non-B hepatitis; chronic myelogenous leukemia; HIV positive, ARC, AIDS (with Retrovir) | Phase II |
| Interleukins | | |
| PEG IL-2 | AIDS (with Retrovir) | Phase I |
| Aldesleukin (IL-2) | Cancer | Phase II/III |
| | Kaposi's sarcoma (with Retrovir) | Phase I |
| Human IL-1 alpha | Bone marrow suppression (chemo/radiotherapy) | Phase I/II |
| Human IL-1 beta | Bone marrow suppression, melanoma, immunotherapy | Phase I/II |
| | Wound healing | Phase II |
| Human IL-2 | Cancer immunotherapy | Phase II |
| Human IL-2 | Cancer immunotherapy | Phase II |

TABLE 2-continued

BIOTECHNOLOGY DRUGS IN DEVELOPMENT

| Approved Drugs Product Type | Abbreviated Indication | U.S. Status |
|---|---|---|
| Human IL-3 | (with Roferon-A) Bone marrow failure, platelet deficiencies, autologous marrow transplant, chemotherapy adjuvant | Phase I/II |
| Human IL-4 | Immunodeficient disease, cancer therapy, vaccine adjuvant immunization | Phase I/II |
| Human IL-4 | Cancer immunomodulator | Phase II |
| Human IL-6 | Platelet deficiencies | Phase I |
| Tumor necrosis factors | | |
| TNF | Cancer | Phase II |
| TNF | Cancer | Phase II |
| Others | | |
| Anakinra (IL-1 receptor antagonist) | AML, CML, inflammatory, rheumatoid arthritis, sepsis, septic shock | Phase II |
| Disaccharide tripeptide glycerol Dipalmitoyl (macrophage activator) | Metastatic colorectal cancer to the liver | Phase II |
| Monophosphoryl lipid A | Gram-negative septic shock | Phase I |
| MTP PE | Osteogenic sarcoma | Phase III |

6. Neurotrophic Proteins

A preferred group of neurologically active compounds for use in the present conjugate is a group of proteins that are generally referred to as neurotrophic proteins. These include nerve growth factor itself (NGF), brain-derived neurotrophic factor (BDNF), neurotrophin-3 (NT-3), neurotrophin-4 (NT-4), neurotrophin-5 (NT-5), insulin-like growth factors (IGF-I and IGF-II), glial cell line derived neurotrophic factor (GDNF), fibroblast growth factor (FGF), ciliary neurotrophic factor (CNTF), epidermal growth factor (EGF), glia-derived nexin (GDN), transforming growth factor (TGF-α and TGF-β), interleukin, platelet-derived growth factor (PDGF) and S100β protein, as well as bioactive derivatives and analogues thereof. Representative classes of this class are listed on Table 3, below.

TABLE 3

NEUROTROPHIC PROTEINS

| Neurotrophic Proteins | References |
|---|---|
| Neuronal Growth Factor (NGF) | Johnston et al., Neurochem. Res., 12, 985–994 (1987); Meakin et al., Trends Neurosci., 15, 323–331 (1992); Koliatsos et al., Ann. Neurol., 30, 831–840 (1991); Hefti et al., Neurobiol. Aging, 10, 515–533 (1989); and Williams et al., Proc. Natl. Acad. Sci. USA, 83, 9231–9235 (1986) |
| Brain-Derived Neurotrophic Factor (BDNF) | Koliatsos et al., Neuron 359–367 (1993); Yan et al., Nature, 360, 753–755 (1992); Hyman et al., Nature, 350, 230–233 (1991); Sendtner et al., Nature, 360, 757–759 (1992); Knüsel et al., J. Neurosci., 12, 4391–4402 (1992); and Hohn et al., Nature, 344, 339–341 (1990) |
| Neurotrophin-3 | Maisonpierre et al., Science, 247, 1446–1451 (1990); Lohof et al., Nature, 363, 350–353 (1993); Kalcheim et al., Proc. Natl. Acad. Sci. USA, 89, 1661–1665 (1992); Dechant et al., J. Neurosci., 13, 2610–2616 (1993); Callazo et al., Neuron, 9, 643–646 (1992); Wong et al., Eur. J. Neurosci., 5, 466–474 (1993); Ip et. al., Neuron, 10, 137–149 (1993) |
| Neurotrophin-4 | Ibanez et al., Development, 117, 1345–1353 (1993); Ip et al., Proc. Natl. Acad. Sci. USA, 89, 3060–3064 (1992); Wong et al., Eur. J. Neurosci., 5, 466–474 (1993); and Ip et. al., Neuron, 10, 137–149 (1993) |
| Neurotrophin-5 | Berkemeier et al., Neuron, 7, 857–866 (1991); Wong et al., Eur. J. Neurosci., 5, 466–474 (1993); and Ip et. al., Neuron, 10, 137–149 (1993) |
| Insulin-like Growth Factors: Insulin-like Growth Factor I (IGF-I), and Insulin-like | Fernyhough et al., Brain Res., 607, 117–124 (1993); Araujo et al., Brain Res., 484, 130–138 (1989); Near et al., Proc. Natl. Acad. Sci. USA, 89, 11716–11720 (1992); Gluckman et al., Biochem. Biophys. Res. Commun., |

TABLE 3-continued

NEUROTROPHIC PROTEINS

| Neurotrophic Proteins | References |
| --- | --- |
| Growth Factor II (IGF-II) | 182, 593–599 (1992); Carson et al., Neuron, 10, 729–740 (1993); and Baskin et al., Trends Neurosci., 11, 107–111 (1988) |
| Glial Cell-Line Derived Neurotrophic Factor (GDNF) | Lin et al., Science, 260, 1130–1132 (1993) |
| Fibroblast Growth Factor (a-FGF, b-FGF) | Sasaki et al., Neurochem. Int., 21, 397–402 (1992); Cummings et al., Brain Res., 591, 271–276 (1992); Wanaka et al., Neuron, 5, 267–281 (1990); Unsicker et al., Ann. N.Y. Acad. Sci., 638, 300–305 (1991); and Enokido et al., Brain Res., 599, 261–271 (1992) |
| Ciliary Neurotrophic Factor (CNTF) | Clatterbuck et al., Proc. Natl. Acad. Sci. USA, 90, 2222–2226 (1993); Louis et al., Science 259, 689–692 (1993); Apfel et al., Brain Res., 604, 1–6 (1993); Ip et al., J. Physiol-Paris, 85, 123–130 (1991); and Ip et al., Eur. J. Neurosci., 5, 25–33 (1993) |
| Epidermal Growth Factor (EGF) | Hefti et al., Neurobiology of Aging, 10, 5125 (1989); Morrison, J. Neurosci. Res., 17, 99 (1987); Morrison et al., J. Neurosci. Res., 21, 71 (1988); Fallon et al., Science, 224, 1107 (1984); Gomex-Pinilla, Brain Res., 438, 385 (1988); and Lakshmanan et al., J. Neurochem., 46, 1081 (1986) |
| Glia-derived Nexin (GDN) | Guenther et al., EMBO J., 4, 1963 (1985); Sommer et al., Biochemistry, 26, 6407 (1987); Gloor et al., Cell, 47, 687 (1986); Rosenblatt et al., Brain Res., 415, 40 (1987); and Reinhard et al., Neuron, 1, 387 (1988) |
| Transforming Growth Factor (TGF-α, TGF-β) | Derynck, Cell, 54, 593 (1988); Wilcox et al., J. Neurosci., 8, 1901 (1988) |
| Interleukins (Interleukin-1, Interleukin-2) | Geulian et al., Science, 228, 497 (1985); Nieto-Sampedro, J. Neurosci. Res., 17, 214 (1987); Lindholm et al., Nature, 230, 658 (1987); Nieto-Sampedro et al., Neurochem. Res., 12, 723 (1987); and Benveniste et al., Neuroimmunol., 17, 301 (1988) |
| Platelette-derived Growth Factor (PDGF) | Mellstrom et al., Muscle Res. Cell Motil., 4, 589 (1983) |
| S100β Protein | Kligman et al., PNAS USA, 82, 7136 (1985) |

B. Carrier Molecules

Proteins with high permeability coefficient-surface area product (PS) values across the blood nerve and blood brain barrier, that are useful in the present method, can be separated into two groups. The first group has PS values that range from $1-10 \times 10^{-6}$ ml/g/sec, which include hemoglobin, lysozyme, cytochrome c, and ceruloplasmin (Tables 4 and 5). The second group has PS values that exceed $10 \times 10^{-6}$ ml/g/sec and include calmodulin, ubiquitin and substance P (Tables 6 and 7). While it might be preferred to use proteins that have the highest PS values as carriers of neurologically active agents, proteins that have PS values in the lower range may be useful clinically because of the characteristics of the individual proteins.

1. Proteins with PS Values from $1-10 \times 10^{-6}$ ml/g/sec

Hemoglobin is the oxygen-carrying protein in vertebrates and consists of four polypeptides, each with a separate tightly bound heme group, a substituted porphyrin with a central iron atom. The ferrous (+2) state of heme binds oxygen, whereas the ferric (+3) state does not. In addition to oxygen, hemoglobin also transports hydrogen (H+) and $CO_2$, with the binding of these molecules regulated by allosteric interactions between its alpha and beta subunits. Thus, the coupling of therapeutic agents to hemoglobin in a way such that its transport across these barriers is not affected promises to be an efficient way of getting said therapeutic agents into the nervous system. Further review of hemoglobin can be found by Dickerson et al., in "Hemoglobin: Structure, Function, Evolution and Pathology", Benjamin and Cummings, 1983.

Lysozyme is a glycosidase which hydrolyzes the glycosidic bond between C-1 of N-acetylmuramate and C-4 of N-acetylglucosamine. It is a relatively small enzyme with a molecular weight of 14.6 kd. Lysozyme from chicken egg white, which is a rich source, is a single polypeptide chain of 129 residues. It is a highly stable protein cross-linked by four disulfide bridges. Since lysozyme functions by cleaving the polysaccharide component of the cell wall of bacteria, it is conceivable that the entry of lysozyme into the endothelial cell may be occurring by way of its enzymatic function whereby it hydrolyzes the glycocalyx of the plasma membrane, in turn facilitating its entry into the endothelial cell. Therefore, conjugating therapeutic agents to lysozyme as a carrier will allow for the efficient delivery of these agents into the nervous system. Further information on lysozyme can be found by Phillips, D. C., Scientific American, 215:78–90, 1966.

Cytochrome c is an electron transport protein which consists of a single polypeptide chain of 104 amino acid residues and a covalently attached heme group. The three-dimensional structure has been elucidated at nearly atomic resolution by Dickerson. (Scientific American 242:137–153, 1980). The protein is spherical with a diameter of 35 angstroms, and the heme group is surrounded by tightly packed, hydrophobic side chains. Cytochrome c carries electrons from the cytochrome reductase complex to cytochrome oxidase. While, it is not clear why cytochrome c has a relatively high permeability across the blood nerve and blood brain barrier, it is this property that results in its usefulness with regard to carrying therapeutic agents into the nervous system.

Ceruloplasmin is a blue copper-containing protein isolated from serum that contains 90% if not all of the copper in serum. It is an alpha-globulin with a molecular weight of about 150,000 and contains 8 atoms of copper. In the rare inherited Wilson's disease, which is primarily a disorder of copper metabolism, there is a marked decrease in plasma ceruloplasmin concentration and an increased level of copper in the liver and brain with associated neurological changes and liver damage. The suggested function of ceruloplasmin is to reversibly release and bind copper at various sites in the body, thereby, regulating the absorption of copper. It plays a critical role in modulating copper concentrations in the nervous system, and, hence, the relatively high PS values identified demonstrate the usefulness of ceruplasmin as a carrier protein for the delivery of therapeutic agents into the nervous system.

2. Proteins with PS Values that exceed $10 \times 10^{-6}$ ml/g/sec

As shown in Tables 6 and 7, a second group of proteins that have high PS values in excess of $10 \times 10^{-6}$ ml/g/sec include calmodulin, ubiquitin, and substance P. The remarkable high PS values found for these three proteins would make them leading candidates as carriers for therapeutic agents into the nervous system.

Calmodulin is a ubiquitous, multifunctional calcium binding protein with a molecular weight of 17 kd that mediates $Ca^{++}$ signaling in many cells and tissues. Calmodulin acts as a $Ca^{++}$ dependent regulator of cyclic nucleotide metabolism, $Ca^{++}$ transport, protein phosphorylation-dephosphorylation cascades, ion transport, cytoskeletal function, and cell-proliferation. It activates isozymes of enzymes, such as adenylyl cyclase, cyclic nucleotide phosphodiesterase, $Ca^{++}$, $Mg^{++}$, ATPase, calcineurin, nitric oxide synthetase, and several protein kinases. It binds to a number of predominantly cytoskeletal proteins, including microtubule associated protein-2(MAP2), fodrin, (spectrin), myristoylated alanine-rich C kinase substrate, neuromodulin, neurogranin, caldesmon, adducin, tau, and tubulin. Calmodulin may function, therefore, in restructuring cytoskeletal processes, such as vesicular or protein transport, or secretion, that results from initial neurotransmitter or hormonal stimulation. This could, in turn, result in efficient intra-cellular transport of calmodulin and its conjugated therapeutic agent through the endothelial cell and into the brain parenchyma, and thus make it a useful carrier molecule in the present invention. A recent review of known functions of calmodulin can be found by Gnegy (*Annual Review of Pharmacology and Toxicology*, 32, 45–70, 1993).

Another protein with a high PS value is ubiquitin which is involved in the major pathway for protein degradation in eukaryotes. Substrate-specific ubiquitin-conjugating enzymes and accessory factors recognize specific signals on proteolytic substrates and attach ubiquitin to defined lysine residues of substrate proteins. These ubiquitin-protein conjugates are then degraded by the proteasome, a multicatalytic protease system which is highly selective and tightly regulated. This pathway mediates the elimination of abnormal proteins and controls the half-lives of certain regulatory proteins. By conjugating ubiquitin to therapeutic agents on appropriate amino acid residues of ubiquitin, this protease complex can be utilized to separate ubiquitin from the agent. This would allow the efficient delivery of the agent into the endothelial cell and utilize the degradative pathways present to separate the ubiquitin from the therapeutic agent. Recent references on ubiquination can be found by Finley and Chau in the *Annual Review of Cell Biology*, 1991,725–69 and by Hershko and Ciechanover in *Annual Reviews of Biochemistry*, 61,761, 1992,.

The protein that has the highest PS values discovered to date is substance P, a naturally occurring tachykinin peptide isolated from brain tissues and gastrointestinal tract. Substance P and its receptors are widely distributed in the CNS and PNS and play many important roles. In the CNS, it controls dopamine neurons in the substantia nigra and ventral tegmental area, cholinergic neurons in the basal forebrain nuclei and norepinephrine neurons in the locus coeruleus so that substance P is likely implicated in many psychoneurological diseases. Consequently, it has been proposed that a number of diseases including Parkinson's, Alzheimer's, and ALS result primarily from a loss of trophicpeptidergic neurotransmitters, including substance P. It is involved in respiratory and cardiovascular controls in the solitary nucleus, in the autonomic nervous system, and in parasympathetic nuclei. It may also play a role in primary afferent neurons in inflammation and allergy reaction. Furthermore, substance P is involved in functions in the c afferent neurons involved in the motor or secretory controls of peripheral organs such as the intestines and salivary glands. Finally, substance P binds to the NK1 receptor and has been implicated in the transmission of pain, as well as in physiological responses such as salivary gland secretion and neurogenic information. The specific targeting of substance P to these appropriate neuronal targets would allow for the direct transmission of therapeutic agents coupled to the substance P to discrete populations of neurons within both the peripheral and central nervous systems. For recent reviews, see Otsuka and Yoshioka, *Physiological Reviews*, 73, 229 1993.

C. Protein Conjugation and Cross-Linking to Therapeutic Agents

There are many approaches for the chemical cross-linking or "conjugation" of proteins. Significant advancement in the application of these cross-linking agents has led to the synthesis of cleavable bifunctional compounds. There are over 300 cross-linkers now available, and it is clear to one of skill in the art that multiple approaches can be used to chemically cross-link therapeutic agents to carrier proteins. In the method of the present method, the conjugation or cross-linking of a therapeutic agent to one of the above-mentioned carrier molecules can be accomplished in a manner so that the ability of the carrier molecule to bind to its receptor is not significantly altered, nor is the bioactivity of the therapeutic agent significantly affected by the cross-linking procedure.

Numerous considerations, such as reactivity, specificity, spacer arm length, membrane permeability, cleavability and solubility characteristics need to be evaluated when choosing an appropriate cross-linker. A recent review of the "Chemistry of Protein Conjugation and Cross-Linking" can be found by Shan S. Wong, CRC Press, Ann Arbor, 1991. The most important question, perhaps, is what functional groups are available for coupling. These functional groups must not be involved in the binding to the receptor or the inactivation of the therapeutic agent. For example, if only lysines or N-terminal are available, a logical choice would be NHS-ester homobifunctional cross-linkers. If one molecule has lysines and the other sulfhydryls, a maleimide NHS-ester cross-linker would be an appropriate choice. If only lysines are available on both molecules, modification to introduce sulfhydryls via the lysines on one molecule would allow for sequential coupling. If both molecules have free sulfhydryls, a homobifunctional sulfhydryl reactive cross-linker would be appropriate. If carboxyls and amines are available, carbodiimide works well. Furthermore, if there are no readily reactive groups, a photoactivatible cross-linker can be used. If lysines are important for the functionality of the molecule, then a cross-linker that will couple through sulfhydryls, carboxyls, or nonspecifically can be used.

To preserve the receptor binding capacity of the carrier, as well as its bioactivity, it may be necessary to choose an appropriate spacer arm length between a cross-linker and the carrier. Similarly, if solubility is a problem and organic solvents are detrimental to the carrier or therapeutic agent, then there are many commercially available water soluble cross-linkers, such as the sulfonated NHS-ester homo- and heterobifunctional cross-linkers.

Conjugation or coupling reagents have at least two reactive groups and can be either homobifunctional with two identical reactive groups or heterobifunctional with two or more different reactive groups. Trifunctional groups also exist and can contain three functional groups. Most homobifunctional cross-linkers react with primary amines commonly found on proteins. Other homobifunctional cross-linkers couple through primary sulfhydryls. Homobifunctional cross-linkers can be used in a one step reaction procedure in which the compounds to be coupled are mixed and the cross-linker is added to the solution. The resulting cross-linking method may result in self-conjugation, intermolecular cross-linking, and/or polymerization. The following are examples of suggested cross-linking approaches and are not meant to be inclusive.

Imido esters are the most specific acylating reagents for reaction with the amine groups whereby in mild alkaline pH, imido esters react only with primary amines to form imidoamides. The product carries a positive charge at physiological pH, as does the primary amine it replaces and therefore, does not affect the overall charge of the protein.

Homobifunctional N-hydroxysuccinimidyl ester conjugation is also a useful cross-link approach to crosslink amine-containing proteins. Homobifunctional sulfhydyl reactive cross-linkers include bismaleimidhexane (BMH), 1,5-difluoro-2,4-dinitrobenzene (DFDNB), and 1,4-di-(3',2'-pyridyldithio) propionamido butane (DPDPB).

Many heterobifunctional cross-linkers are commercially available with the majority containing an amine-reactive functional group on one end and a sulfhydryl-reactive group on the other end. Multiple heterobifunctional haloacetyl cross-linkers are available, as are pyridyl disulfide cross-linkers. In addition, heterobifunctional cross-linking reagents which react with carboxylic groups involves the carbodiimides as a classic example for coupling carboxyls to amines resulting in an amide bond.

D. Dosage Forms/Modes of Administration

This invention also provides pharmaceutical compositions suitable for administration to animals to increase the permeability of the blood-brain barrier or blood-nerve barrier to a molecule of interest. Such compositions will comprise an effective amount of the conjugate in combination with a pharmaceutically acceptable carrier. The carrier may be a liquid, so that the composition is adapted for parenteral administration, or may be solid, i.e., a capsule shell plus vehicle, a tablet, a pill and the like, formulated for oral administration. Furthermore, the carrier may be in the form of a nebulizable liquid or solid so that the composition is adapted for inhalation. When administered parenterally, the composition should be pyrogen free and in an acceptable parenterally acceptable carrier having due regard for pH, isotonicity, and stability. Briefly, dosage formulations of the conjugate of the present invention are prepared for storage or administration by mixing the compound having the desired degree of purity with physiologically acceptable carriers, exipients, or stabilizers.

An effective amount of the carrier molecule is that amount which will significantly increase the blood-brain barrier permeability for the neuroactive compound of interest. In other words, it will increase the permeability of the blood-brain barrier to allow sufficient quantities of the neuroactive compound of interest to pass from the blood to the interstitial fluid of the brain or nerve to exert a therapeutic or prophylactic effect or allow diagnostic procedures. The effective amount will be determined on an individual basis and will be based, at least in part, on consideration of the individual's size, age, the specific state or disease to be treated, the severity of the symptoms to be treated, the result sought, the specific carrier molecule used, and other variations among hosts, etc. Thus, the effective amount can be determined by one of ordinary skill in the art employing such factors and using no more than routine experimentation. In general, about 0.5 to 1000 mg of the conjugate is compounded with a physiologically acceptable vehicle, carrier, excipient, binder, preservative, stabilizer, etc., as called for by accepted pharmaceutical practice to yield a pharmaceutical unit dosage form.

Typical adjuvants which may be incorporated into tablets, capsules and the like are binders, excipients, disintegrating agents, lubricants, sweetening agents and flavoring agents. When the dosage form is a soft gelatin capsule, in addition to the above materials it may also contain a liquid carrier such as a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as water or a naturally occurring vegetable oil like sesame, peanut, or cottonseed oil or a synthetic fatty vehicle like ethyl oleate or the like may be desired. Buffers preservatives, antioxidants and the like can be incorporated according to accepted pharmaceutical practice.

Sustained release compositions also include liposomally entrapped conjugates. Liposomes containing the conjugate are prepared by known methods. See Epstein et al., *PNAS U.S.A.*, 82, 3688 (1985) and Hwang et al, *PNAS U.S.A.*, 77, 4030 (1980). Ordinarily the liposomes are of the small (about 200–800 angstroms) unilamellar type in which the lipid content is greater than about 30 mol. % cholesterol, the selected proportion being adjusted for the optimal neurologically active agent therapy.

The dosage will be determined by the attending physician taking into account various factors known to modify the action of drugs including severity and type of disease, body weight, sex, diet, time and route of administration, other medications and other relevant clinical factors. Typically, the daily regime will range from about 1–3000 µg/kg body weight. Preferably the dosage will range from about 10–1000 µg/kg body weight. Most preferably, the dosage will range from about 50–150 mg/day. Therapeutically effective dosages may be determined by either in vitro or in vivo methods.

The increase in permeability of the blood-brain or blood-nerve barrier in response to the carrier molecule relates not only to the quantity of molecules passing from the blood to the brain, but also, to the type of molecule of interest. The effect of the carrier molecule is to preferentially increase the passage of small molecular weight substances through the blood-brain or blood-nerve barrier.

The present invention also provides a kit comprising the above-mentioned composition packaged with instructions for its use. This packaging will preferably include the composition in unit dosage form suitable for intravenous injection or infusion. This packaging will also include instructions for administration of the composition by the user in the form of a tag or package insert.

The invention will be further described by reference to the following detailed examples.

Animals and Reagents. Male Sprague-Dawley rats (24-weeks-old) (460–500 g) were obtained from Bio Lab (St. Paul) and were used to determine the PS and $V_p$ measurements. All animals were kept for a minimum of 3 days under standard housing conditions and feeding schedules prior to the experiments. Human ALB was isolated from normal human plasma using CM-Affi-Gel Blue (Bio-Rad) and further subjected to boronate affinity chromatography to remove the glycated species. Calmodulin, ubiquitin, lysozyme, hemoglobin, cytochrome c, substance P, and ceruloplasmin were all obtained from Sigma Chemical Co., St. Louis, Mo. Carrier-free sodium $^{125}I$ and sodium $^{131}I$ were obtained from Amersham. Protein concentrations were determined by the BCA protein assay procedure of Smith et al. (*Anal. Biochem.*, 150, 76–85 (1985)) using the Pierce Assay Kit with BSA as the standard.

Protein Radioiodination. Aliquots of the proteins were labeled with $^{125}I$ and $^{131}I$ using the chloramine-T method as described previously by Poduslo et al., *Proc. Natl. Acad Sci. U.S.A.*, 85, 4879 (1988). Free radioactive iodine was separated from the radiolabeled protein by dialysis against 0.2M NaI. Purity of the radiolabeled proteins was determined by paper chromatography as described by Poduslo et al., *J. Neurosci.*, 2, 1507 (1982). The radiolabeled protein that stayed at the origin was always greater than 99% of the total radioactivity. The radioiodinated proteins were evaluated by SDS-PGE as previously described by Poduslo, *Anal. Biochem.*, 114, 131 (1981). No degradative products were found after iodination or after PS/$V_p$ measurements were made.

EXAMPLE 1

PS and $V_p$ Measurements of Radioiodinated Carrier Molecules

The experimental protocol employed was based on the methods of Ohno et al. *Am. J. Physiol.*, 235, H299–H307 (1978) and Rapoport et al., *Brain Res.*, 172, 354–359 (1979) with modifications as described by Poduslo et al., *PNAS U.S.A.*, 89, 2218–2222 (1992). Briefly, a bolus of PBS containing $^{125}I$ labelled carrier molecule was injected rapidly into the catheterized brachial vein of pentobarbital anesthetized rats. Blood was sampled during the next 30, 60, or 240 minutes from the brachial artery, depending on the carrier molecule being evaluated. Prior to the sacrifice of the animal at time sequences of 60 or 120 seconds, the second isotope-labelled carrier molecule ($^{131}I$) was administered intravenously to serve as the residual plasma volume indicator ($V_p$).

After the final blood sample was collected, the sciatic nerves were rapidly removed and desheathed. Similarly, the brain was removed followed by the meninges. The brain was dissected into the cortex, caudal putamen, hippocampus, thalamus, brain stem, and cerebellum. The tissue was then lyophilized, and the dry weight was determined with a microbalance. These weights were then converted to their respective wet weights with wet weight/dry weight ratios previously determined for desheathed rat sciatic nerve and for the different brain regions. Tissue and plasma samples were assayed for $^{125}I$ and $^{131}I$ radioactivity in a 2-channel gamma counter. Radioactivity was corrected for crossover of $^{131}I$ activity into the $^{125}I$ channel and background activity. The $V_p$ and PS measurements were calculated as described previously in Poduslo et al., *Proc. Natl. Acad. Sci. U.S.A.*, 89, 2218 (1992). Albumin was also evaluated in the same manner to provide for a baseline with which to review the results of the carrier molecules (See Table 8), since albumin is the major protein of the endoneurial fluid as well as a prominent protein in the ventricle, cistern, and lumbar spinal fluid. Poduslo et al., *Brain Res.*, 332, 95 (1985), Rapoport, in Neurobiology of Cerebrospinal Fluid, 2, Wood, J. H., ed. (Plenum Press, New York), pp. 233–245. Statistical evaluations were done using Student's two-tailed paired t-test. Significance was accepted at the $p<0.05$ level.

PS and $V_p$ Measurements of the BNB

The PS and $V_p$ values obtained for hemoglobin, lysozyme, cytochrome c and ceruloplasmin across the blood nerve barrier (BNB) are found in Table 4. Each of the carrier molecules tested had PS measurements at least 65 times that attainable with albumin. No changes were observed in the residual plasma volume ($V_p$) for any of the carrier molecules compared to albumin, which indicates that the vascular volume did not change during the course of the experiment. Since the residual plasma volume ($V_p$) is a useful indicator of S (capillary surface area), the observed changes in PS with little changes in vascular volume allow for a direct assessment of capillary permeability of the carrier molecule.

The PS and $V_p$ values obtained for calmodulin, ubiquitin and substance P across the blood nerve barrier (BNB) are found in Table 6. Each of the carrier molecules tested had PS measurements at least 200 times that attainable with albumin, with substance P exhibiting a relative increase of 856 over the PS value of albumin. Similarly, there was no change in the $V_p$, except for substance P, whose increase reflected the fast plasma half-life which was of the same time scale used to measure the residual plasma volume of this protein.

PS and $V_p$ Measurements of the BBB

Five different brain regions were evaluated for their PS and $V_p$ values across the BBB for hemoglobin, lysozyme, cytochrome c and ceruloplasmin with the results shown in Table 5. The same evaluation was carried out with calmodulin, ubiquitin and substance P with the resulting data shown in Table 7. In general, the PS values for the evaluated carrier molecules were higher than that of albumin by at least a multiple of 18. In general, little changes in $V_p$ values for the carrier molecules were observed.

The PS values for substance P in the different brain regions ranged from $27.68 \times 10^{-6}$ to $36.53 \times 10^{-6}$ ml/g/s with the lowest PS value observed in the cortex and the highest values obtained in the thalamus. This resulted in a relative increase of 183.3 to 623.6 fold compared to albumin. This relative increase in PS of substance P versus albumin were all highly significant ($p=0.0002$ to $0.0115$). The $V_p$ values for substance P ranged from 11.03 µl/g to 21.29 µl/g resulting in a relative increase of 1.2 fold to 2.9 fold compared to albumin. Again, this change in $V_p$ reflected the fast plasma half-life of this neuropeptide.

All of the patents, patent documents and publications cited herein are incorporated by reference.

The invention has been described with reference to various specific and preferred embodiments and techniques. However, it should be understood that many variations and modifications may be made while remaining within the spirit and scope of the invention.

TABLE 4

PERMEABILITY COEFFICIENT-SURFACE AREA PRODUCT (PS) AND RESIDUAL ENDONEURIAL PLASMA VOLUME ($V_p$) OF THE BLOOD NERVE BARRIER FOR HEMOGLOBIN (HEM), LYSOZYME (LYS), CYTOCHROME c (CYTOC), AND CERULOPLASMIN (CER)

| | HEM | Relative Increase HEM vs ALB | LYS | Relative Increase LYS vs ALB | CYTOC | Relative Increase CYTOC vs ALB | CER | Relative Increase CER vs ALB |
|---|---|---|---|---|---|---|---|---|
| PS: ml/g/sec × $10^6$ | 6.60 ± 1.33 | 65.3 | 6.71 ± 1.65 | 66.4 | 7.43 ± 3.68 | 73.6 | 8.32 ± 1.06 | 82.4 |
| $V_p$: µl/g | 1.91 ± 0.35 | 1.0 | 2.57 ± 0.52 | 1.3 | 1.96 ± 0.32 | 1.0 | 1.98 ± 0.38 | 1.0 |

$\bar{x}$ ± SD
HEM: n = 10
LYS: n = 12
CYTOC: n = 14
CER: n = 12

TABLE 5

PERMEABILITY COEFFICIENT-SURFACE AREA PRODUCT (PS) AND RESIDUAL BRAIN PLASMA VOLUME ($V_p$) OF THE BLOOD BRAIN BARRIER FOR HEMOGLOBIN (HEM), LYSOZYME (LYS), CYTOCHROME c (CYTOC), AND CERULOPLASMIN (CER)

| | HEM | Relative Increase HEM vs ALB | LYS | Relative Increase LYS vs ALB | CYTOC | Relative Increase CYTOC vs ALB | CER | Relative Increase CER vs ALB |
|---|---|---|---|---|---|---|---|---|
| PS: ml/g/sec × $10^6$ | | | | | | | | |
| Cortex | 4.89 ± 1.00 | 32.4 | 4.09 ± 0.65 | 27.1 | 4.76 ± 1.76 | 31.5 | 2.79 ± 1.38 | 18.5 |
| Caudo Pulamen | 5.25 ± 1.04 | 56.5 | 4.65 ± 1.16 | 50.0 | 5.30 ± 2.54 | 57.0 | 3.14 ± 1.51 | 33.8 |
| Hippocampus | 5.59 ± 1.28 | 57.6 | 5.22 ± 0.74 | 53.8 | 5.70 ± 2.27 | 58.8 | 2.90 ± 0.90 | 29.9 |
| Thalmus | 6.70 ± 1.46 | 81.7 | 6.08 ± 1.21 | 74.1 | 7.00 ± 2.64 | 85.4 | 3.44 ± 1.62 | 42.0 |
| Brain Stem | 7.31 ± 2.02 | 126.0 | 7.12 ± 1.72 | 122.8 | 7.51 ± 2.88 | 129.5 | 4.33 ± 2.02 | 74.7 |
| Cerebellum | 7.21 ± 1.56 | 70.7 | 6.68 ± 1.18 | 65.5 | 7.10 ± 2.41 | 69.6 | 4.32 ± 2.21 | 42.4 |
| $V_p$: µl/g | | | | | | | | |
| Cortex | 6.17 ± 0.95 | 0.7 | 6.34 ± 0.93 | 0.7 | 5.60 ± 1.13 | 0.6 | 4.28 ± 0.46 | 0.5 |
| Caudo Pulamen | 5.94 ± 0.95 | 0.7 | 6.38 ± 1.23 | 0.8 | 5.32 ± 1.28 | 0.7 | 3.97 ± 0.23 | 0.5 |
| Hippocampus | 7.32 ± 0.53 | 0.9 | 7.68 ± 1.14 | 0.9 | 6.67 ± 0.97 | 0.8 | 4.17 ± 0.87 | 0.5 |
| Thalmus | 11.33 ± 2.47 | 1.4 | 10.37 ± 1.67 | 1.3 | 10.07 ± 2.62 | 1.3 | 5.69 ± 0.77 | 0.7 |
| Brain Stem | 12.72 ± 3.92 | 1.7 | 14.96 ± 3.30 | 2.1 | 12.50 ± 2.93 | 1.7 | 8.93 ± 0.75 | 1.2 |
| Cerebellum | 13.07 ± 4.06 | 1.1 | 13.68 ± 1.85 | 1.1 | 11.44 ± 2.61 | 0.9 | 9.07 ± 1.23 | 0.7 |

$\bar{x}$ ± SE
HEM: n = 5
LYS: n = 6
CYTOC: n = 7
CER: n = 6

TABLE 6

PERMEABILITY COEFFICIENT-SURFACE AREA PRODUCT (PS) AND RESIDUAL ENDONEURIAL PLASMA VOLUME ($V_p$) OF THE BLOOD NERVE BARRIER FOR CALMODULIN (CAL), UBIQUITIN (UB), AND SUBSTANCE P (SP)

| | CAL | Relative Increase CAL vs. ALB | UB | Relative Increase UB vs ALB | SP | Relative Increase SP vs ALB |
|---|---|---|---|---|---|---|
| PS: ml/g/sec × $10^6$ | 21.34 ± 3.40 | 211.3 | 23.12 ± 0.29 | 228.9 | 86.48 ± 4.90 | 856.2 |
| $V_p$: µl/g | 1.66 ± 0.32 | 0.9 | 1.84 ± 0.51 | 0.9 | 14.87 ± 3.53 | 7.6 |

$\bar{x}$ ± SD
CAL: n = 16
UB: n = 12
SP: n = 14

TABLE 7

PERMEABILITY COEFFICIENT-SURFACE AREA PRODUCT (PS) AND RESIDUAL BRAIN PLASMA VOLUME ($V_p$) OF THE BLOOD BRAIN BARRIER FOR CALMODULN (CAL), UBIQUITIN (UB), AND SUBSTANCE P (SP)

|  | CAL | Relative Increase CAL vs. ALB | UB | Relative Increase UB vs ALB | SP | Relative Increase SP vs ALB |
|---|---|---|---|---|---|---|
| PS: ml/g/sec × $10^6$ | | | | | | |
| Cortex | 12.37 ± 4.75 | 81.9 | 13.57 ± 0.25 | 89.9 | 27.68 ± 8.14 | 183.3 |
| Caudo Putamen | 11.00 ± 1.91 | 118.3 | 19.72 ± 0.88 | 212.0 | 33.06 ± 10.08 | 355.5 |
| Hippocampus | 12.41 ± 2.17 | 127.9 | 15.58 ± 0.18 | 160.6 | 32.21 ± 10.07 | 332.1 |
| Thalamus | 14.15 ± 2.36 | 172.6 | 17.47 ± 0.31 | 213.0 | 36.53 ± 11.11 | 445.5 |
| Brain Stem | 15.76 ± 3.73 | 271.7 | 21.32 ± 0.36 | 367.6 | 36.17 ± 8.54 | 623.6 |
| Cerebellum | 15.74 ± 2.25 | 154.3 | 20.92 ± 0.34 | 205.1 | 35.48 ± 9.30 | 347.8 |
| $V_p$: µl/g | | | | | | |
| Cortex | 3.82 ± 0.65 | 0.4 | 3.34 ± 0.35 | 0.4 | 11.59 ± 3.19 | 1.2 |
| Caudo Putamen | 3.39 ± 0.65 | 0.4 | 4.33 ± 1.69 | 0.5 | 11.03 ± 3.61 | 1.4 |
| Hippocampus | 3.91 ± 0.71 | 0.5 | 3.83 ± 0.78 | 0.5 | 13.60 ± 4.40 | 1.6 |
| Thalamus | 5.51 ± 0.77 | 0.7 | 5.20 ± 0.91 | 0.7 | 15.30 ± 4.79 | 2.0 |
| Brain Stem | 7.86 ± 1.46 | 1.1 | 8.00 ± 2.42 | 1.1 | 21.29 ± 5.74 | 2.9 |
| Cerebellum | 7.30 ± 1.32 | 0.6 | 7.42 ± 1.25 | 0.6 | 20.23 ± 4.78 | 1.7 |

$\bar{x}$ ± SD
CAL: n = 8
UB: n = 6
SP: n = 7

TABLE 8

PERMEABILITY COEFFICIENT-SURFACE AREA PRODUCT (PS) AND RESIDUAL ENDONEURIAL AND BRAIN PLASMA VOLUME ($V_p$) OF THE BLOOD NERVE BARRIER AND BLOOD BRAIN BARRIER FOR ALBUMIN

|  |  | BNB |  | BBB |
|---|---|---|---|---|
| PS: ml/g/sec × $10^6$ | Sciatic Nerve | 0.101 ± 0.088 | Cortex | 0.151 ± 0.035 |
|  |  |  | Caudo Putamen | 0.093 ± 0.069 |
|  |  |  | Hippocampus | 0.097 ± 0.038 |
|  |  |  | Thalamus | 0.082 ± 0.041 |
|  |  |  | Brain Stem | 0.058 ± 0.032 |
|  |  |  | Cerebellum | 0.102 ± 0.056 |
| $V_p$: µl/g | Sciatic Nerve | 1.949 ± 0.589 | Cortex | 9.492 ± 1.550 |
|  |  |  | Caudo Putamen | 7.974 ± 3.133 |
|  |  |  | Hippocampus | 8.395 ± 1.267 |
|  |  |  | Thalamus | 7.846 ± 1.061 |
|  |  |  | Brain Stem | 7.283 ± 2.371 |
|  |  |  | Cerebellum | 12.149 ± 2.276 |

$\bar{x}$ ± SD
ALB:
N = 10 (BNB)
N = 5 (BBB)

What is claimed is:

1. A method to enhance the ability of a neurologically active compound to penetrate the blood nerve barrier (BNB) or blood brain barrier (BBB) comprising parenterally administering to a mammal in need of treatment with said neurologically active compound, a conjugate consisting of an effective amount of said neurologically active compound conjugated to a carrier molecule with a substantial permeability coefficient across the BNB or BBB selected from the group consisting of hemoglobin, lysozyme, cytochrome c, ceruloplasmin, calmodulin, ubiquitin and substance P.

2. The method of claim 1 wherein the neurologically active compound is selected from the group consisting of a compound acting at a synaptic and/or neuroeffector junctional site, a compound acting on the central or peripheral nervous system, or a neurotrophic protein.

3. The method of claim 1 wherein the neurologically active compound is a neurotrophic protein.

4. The method of claim 1 wherein the mammal is a human.

5. The method of claim 1 wherein the carrier molecule is substance P.

6. The method of claim 1 wherein the carrier molecule is calmodulin.

7. The method of claim 1 wherein the carrier molecule is ubiquitin.

8. The method of claim 1 wherein the compound and the carrier molecule are conjugated in a one to one molar ratio.

9. The method of claim 1 wherein said conjugated neurologically active compound is administered in combination with a pharmaceutically acceptable carrier.

10. The method of claim 9 wherein the mode of administration is parenteral administration.

11. The method of claim 9 wherein the mode of administration is oral administration.

12. A pharmaceutical composition comprising a neurologically active compound conjugated to a carrier molecule selected from the group consisting of hemoglobin, lysozyme, cytochrome c, ceruloplasmin, calmodulin, ubiquitin and substance P, in combination with a pharmaceutically acceptable carrier, adapted for parenteral administration.

13. The composition of claim 12 wherein the neurologically active compound is selected from the group consisting of a compound acting at a synaptic and/or neuroeffector junctional site, a compound acting on the central or peripheral nervous system, or a neurotrophic protein.

14. The pharmaceutical composition of claim 12 wherein the neurologically active compound is a neurotrophic protein.

15. The composition of claim 12 wherein the compound and the carrier molecule are conjugated in a one-to-one molar ratio.

16. The composition of claim 12 wherein the pharmaceutically acceptable carrier is a liquid vehicle.

17. The composition of claim 12 wherein the carrier molecule is substance P.

18. The method of claim 12 wherein the carrier molecule is calmodulin.

19. The method of claim 12 wherein the carrier molecule is ubiquitin.

* * * * *